(12) United States Patent
Biedermann et al.

(10) Patent No.: US 11,045,230 B2
(45) Date of Patent: Jun. 29, 2021

(54) COUPLING ASSEMBLY AND POLYAXIAL BONE ANCHORING DEVICE COMPRISING THE SAME

(71) Applicant: BIEDERMANN TECHNOLOGIES GMBH & CO. KG, Donaueschingen (DE)

(72) Inventors: Lutz Biedermann, VS-Villingen (DE); Bernd Fischer, Bräunlingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 19 days.

(21) Appl. No.: 16/518,339

(22) Filed: Jul. 22, 2019

(65) Prior Publication Data

US 2020/0008844 A1   Jan. 9, 2020

Related U.S. Application Data

(63) Continuation of application No. 15/818,351, filed on Nov. 20, 2017, now Pat. No. 10,383,662, which is a
(Continued)

(30) Foreign Application Priority Data

Dec. 10, 2014   (EP) .................................... 14197226

(51) Int. Cl.
*A61B 17/70* (2006.01)
*A61B 17/00* (2006.01)

(52) U.S. Cl.
CPC ...... *A61B 17/7037* (2013.01); *A61B 17/7032* (2013.01); *A61B 2017/00477* (2013.01)

(58) Field of Classification Search
CPC .................. A61B 17/70; A61B 17/7032–7046
See application file for complete search history.

(56) References Cited

U.S. PATENT DOCUMENTS 6,248,105 B1   6/2001   Schlaepfer
6,280,442 B1   8/2001   Barker
(Continued)

FOREIGN PATENT DOCUMENTS

EP          2687172 A1      1/2014
JP       2001-525707 A     12/2001
(Continued)

OTHER PUBLICATIONS

Extended European Search Report and Opinion issued by the EPO for EP 14197226.5 dated Jun. 9, 2015 (7 pages).

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A coupling assembly for coupling a rod to a bone anchoring element is provided, wherein the coupling assembly includes a receiving part having a first end, a second end, a central axis extending through the first end and second end, an accommodation space for accommodating a head of an anchoring element, a bore extending from the accommodation space to the first end, and a recess for receiving a rod. The accommodation space has an opening at the second end sized to permit insertion of a head of the bone anchoring element. The coupling assembly further includes a retainer element configured to be positioned at least partially in the accommodation space and being radially expandable and/or compressible to allow retaining a head inserted through the opening. The retainer element is held in position adjacent the opening by an engagement structure provided at or in the accommodation space. The coupling assembly further
(Continued)

includes a locking element configured to be arranged at least partially in the accommodation space. The locking element is movable from a first position, in which the retainer element is allowed to expand and release an inserted head, to a second position, in which radial expansion of the retainer element is hindered to prevent release of an inserted head. When the locking element is in the second position, a head of an anchoring element can be locked by exertion of a pressure force directly onto the head to press the head against the retainer element.

20 Claims, 12 Drawing Sheets

Related U.S. Application Data continuation of application No. 14/964,444, filed on Dec. 9, 2015, now Pat. No. 9,848,916.

(60) Provisional application No. 62/090,242, filed on Dec. 10, 2014.

(56) References Cited

U.S. PATENT DOCUMENTS

| | | |
|---|---|---|
| 6,485,491 B1 | 11/2002 | Farris |
| 8,197,517 B1 | 6/2012 | Lab |
| 8,556,938 B2 | 10/2013 | Jackson et al. |
| 9,848,916 B2 | 12/2017 | Biedermann et al. |
| 2004/0102781 A1 | 5/2004 | Jeon |
| 2004/0176766 A1 | 9/2004 | Shluzas |
| 2004/0267264 A1 | 12/2004 | Konieczynski |
| 2005/0283157 A1 | 12/2005 | Coates |
| 2006/0276791 A1 | 12/2006 | Shluzas |
| 2007/0270813 A1 | 11/2007 | Garamszegi |
| 2008/0045953 A1 | 2/2008 | Garamszegi |
| 2008/0287998 A1 | 11/2008 | Doubler |
| 2008/0294202 A1* | 11/2008 | Peterson ............ A61B 17/7037 606/305 |
| 2010/0234902 A1 | 9/2010 | Biedermann |
| 2011/0213424 A1 | 9/2011 | Biedermann |
| 2013/0023941 A1 | 1/2013 | Jackson et al. |
| 2013/0096620 A1 | 4/2013 | Biedermann |
| 2013/0103098 A1 | 4/2013 | Jackson et al. |
| 2013/0150852 A1 | 6/2013 | Shluzas |
| 2013/0197586 A1 | 8/2013 | Matthis |
| 2013/0211465 A1* | 8/2013 | Savage ................ A61B 17/866 606/308 |
| 2013/0338721 A1 | 12/2013 | Biedermann |
| 2014/0025119 A1 | 1/2014 | Biedermann |
| 2014/0236239 A1 | 8/2014 | Biedermann |
| 2014/0277157 A1 | 9/2014 | Chandanson |
| 2014/0321945 A1 | 10/2014 | Black |
| 2015/0025579 A1 | 1/2015 | Biedermann |
| 2015/0032162 A1 | 1/2015 | Biedermann |
| 2015/0051651 A1 | 2/2015 | Terrill |
| 2015/0142059 A1 | 5/2015 | Biedermann |
| 2015/0173816 A1 | 6/2015 | Biedermann |
| 2016/0166288 A1 | 6/2016 | Biedermann |
| 2016/0262803 A1 | 9/2016 | Nelson |
| 2016/0361096 A1 | 12/2016 | van der Pol |

FOREIGN PATENT DOCUMENTS

| | | |
|---|---|---|
| JP | 2013-500127 A | 1/2013 |
| JP | 2013-542774 A | 11/2013 |
| WO | WO 98/52482 | 11/1998 |
| WO | WO 2011/043805 A1 | 4/2011 |

\* cited by examiner

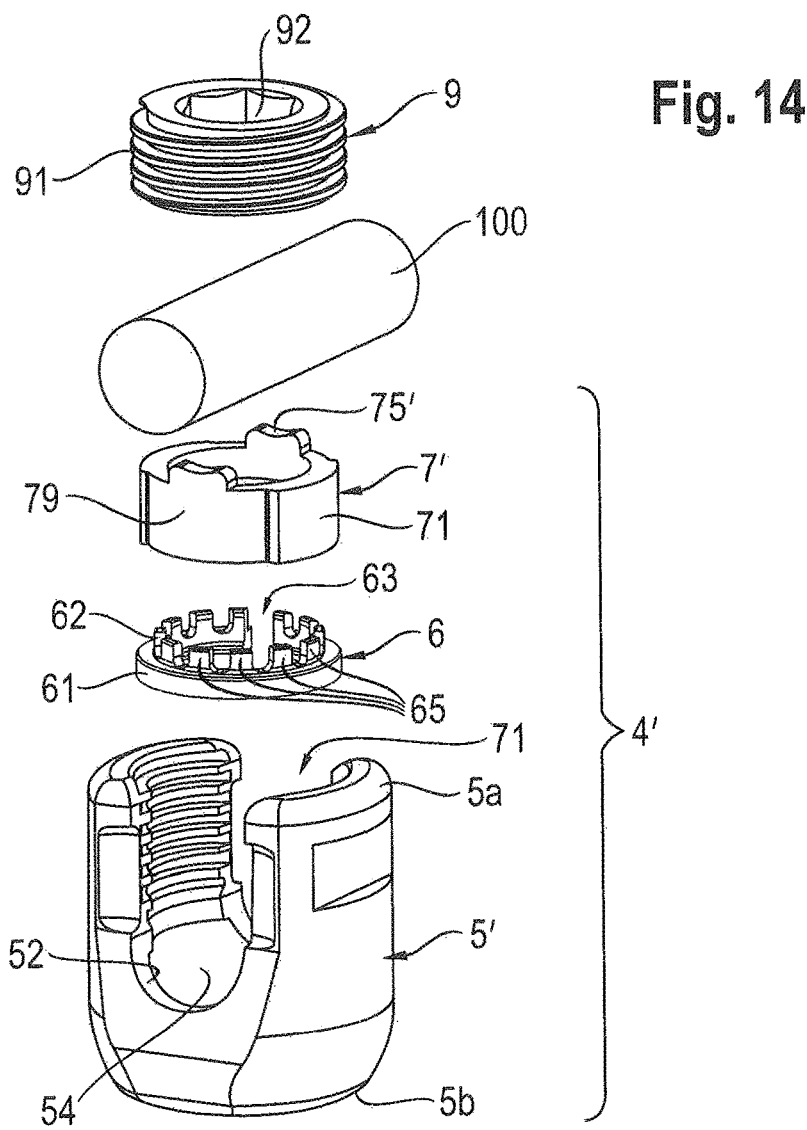
Fig. 14
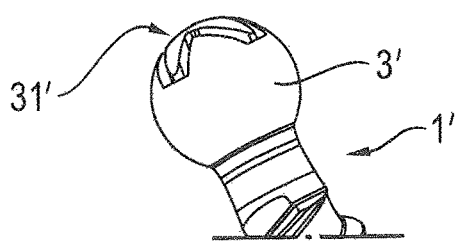
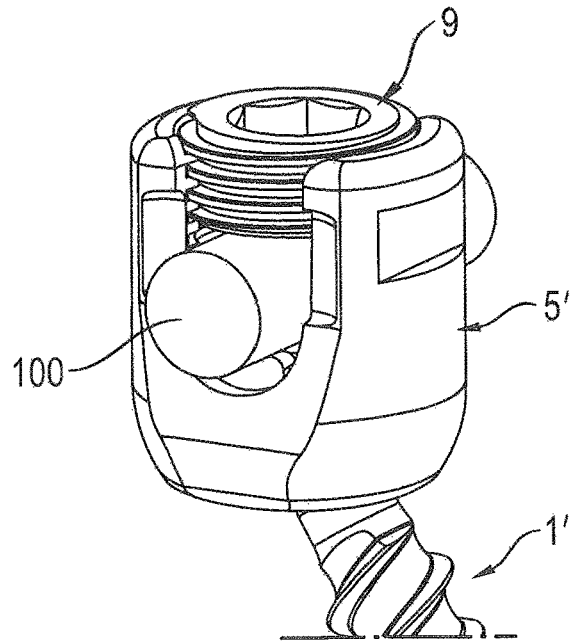
Fig. 15

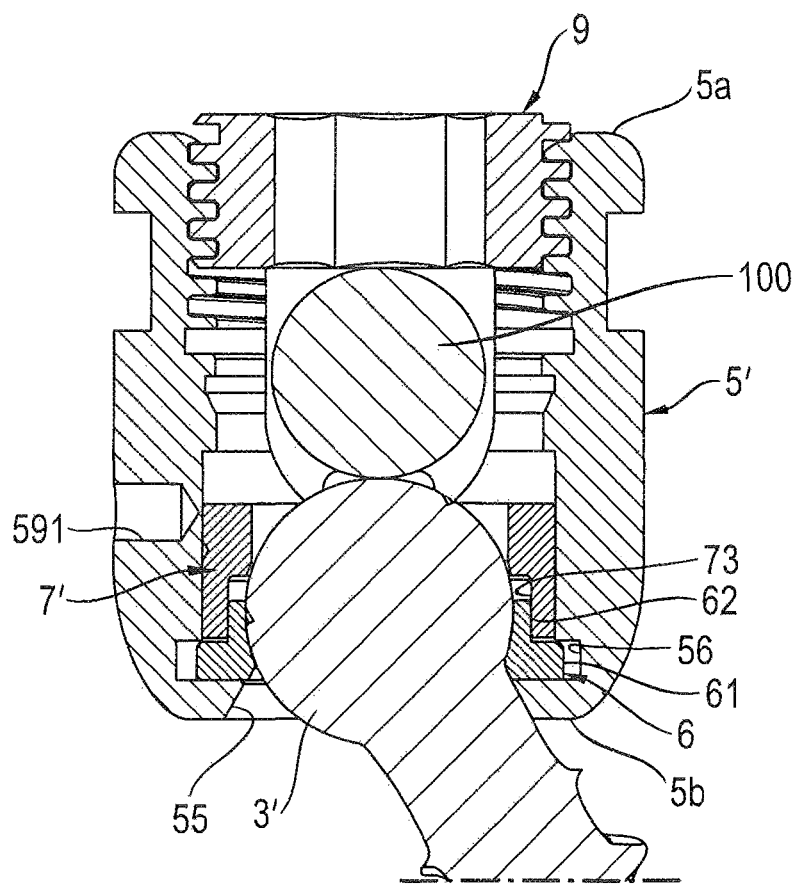
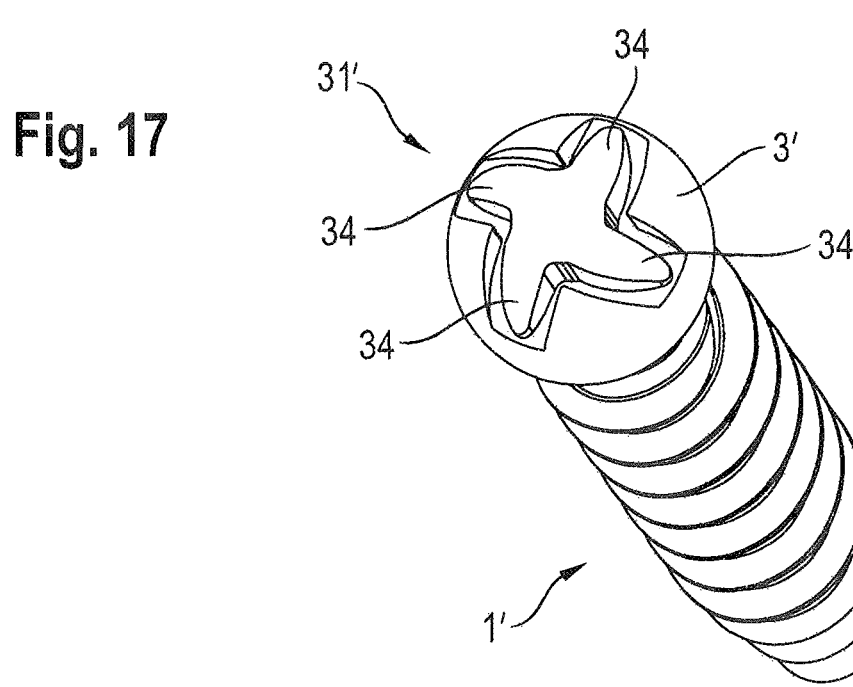

COUPLING ASSEMBLY AND POLYAXIAL BONE ANCHORING DEVICE COMPRISING THE SAME

CROSS-REFERENCE TO RELATED APPLICATIONS

This application is a continuation of U.S. patent application Ser. No. 15/818,351, filed Nov. 20, 2017, which is a continuation of U.S. patent application Ser. No. 14/964,444, filed Dec. 9, 2015, now U.S. Pat. No. 9,848,916, which claims the benefit of U.S. Provisional Application Ser. No. 62/090,242, filed Dec. 10, 2014, the contents of which are hereby incorporated by reference in their entirety, and claims priority from European Patent Application EP 14 197 226.5, filed Dec. 10, 2014, the contents of which are hereby incorporated by reference in their entirety.

BACKGROUND

Field

The present disclosure relates to a coupling assembly for coupling a rod to a bone anchoring element and to a polyaxial bone anchoring device including such a coupling assembly. The coupling assembly includes a receiving part having a channel for receiving the rod, an accommodation space for accommodating a head of a bone anchoring element, and a retainer element for retaining the head of the bone anchoring element in the receiving part. The coupling assembly may also include a pressure element configured to exert a pressure force onto the head of the bone anchoring element. The coupling assembly is configured to receive the head of the bone anchoring element from a bottom opening of the receiving part and the retainer element may, for example, snap onto the head of the bone anchoring element to retain the head in the accommodation space.

Description of Related Art

Document U.S. Pat. No. 6,248,105 B1 discloses a device for connecting a longitudinal rod with a pedicle screw. The device includes a sleeve, a hollow cylindrical insert, and a spring chuck. The spring chuck has annular flanges held in a ring-shaped channel near the bottom opening of the sleeve. The spring chuck has a cavity designed to receive the head of the pedicle screw. When the rod is locked by means of a tension screw, pressure is exerted by the rod onto the insert, which engages the spring chuck by means of respectively complementary conical engaging surfaces. The spring chuck is thereby crush-locked onto the head of the pedicle screw. The flanges of the spring chuck are received in the ring-shaped channel of the sleeve, and thereby the spring chuck is held in the sleeve and the head is retained in the sleeve.

Document U.S. Pat. No. 6,280,442 B1 discloses a multi-axial bone screw assembly. The assembly includes a receiver member, a crown member movably disposed in a lower opening portion of the receiver member, and a retaining member. The retaining member defines an aperture smaller than a width of a head of a bone anchor received therein. The retaining member is housed in a groove of the receiver member. The groove extends around the lower opening portion of the receiver member. The retaining member prevents removal of the head from the lower opening portion. The retaining member has a C-shape with a gap allowing the retaining member to compress to snap into the groove. Once the retaining member is inserted into the groove, the retaining member cannot be further expanded.

Document U.S. Pat. No. 8,556,938 B1 discloses a polyaxial bone screw assembly having a receiver with a lower cavity cooperating with a lower opening. An upper portion of a shank expands a retaining member in the receiver lower cavity to capture the shank upper portion in the receiver. Either the retaining member or an insert provides for a friction-fit of the shank upper portion in the receiver. Final locking of the polyaxial mechanism is provided by frictional engagement between the shank upper portion and the retaining member. A pre-assembled receiver, retaining member and optional insert may be popped or snapped onto the shank upper portion prior to or after implantation of the shank into a vertebra.

SUMMARY

It is an object of the present invention to provide a coupling assembly for retaining a head of a bone anchoring element to be introduced from a bottom opening in the coupling assembly, wherein the reliability and durability as well as the handling of the assembly is improved.

According to an aspect of the invention, a coupling assembly includes a receiving part, a retainer element, and a locking element. The receiving part has an accommodation space with an opening at one end of the receiving part. A head of an anchoring element can be inserted through the opening to be received within the accommodation space. The retainer element is held in position adjacent the opening by an engagement structure provided at or in the accommodation space.

The retainer element is radially expandable and/or compressible, including when held in position by the engagement structure. The retainer element may snap over the head of the anchoring element when the head is inserted through the opening. In order to retain the head in the accommodation space of the receiving part, expansion of the retainer element is prevented or at least hindered by a locking element. According to one embodiment, the locking element partially encompasses an engagement portion of the retainer element in a radial direction to hinder expansion of the retainer element. In a non-locked state, a small amount of play between respective engagement portions of the retainer element and the locking element is possible while a release of the head is impeded. As a consequence, the retainer element is prevented from releasing the head of the anchoring element.

The locking element is configured to move between a first position in the accommodation space, wherein the accommodation space permits the retainer element to expand, and a second position, where the above described radial locking of the retainer element takes place. In the second position, when the head of the anchoring element is locked in a final state, a pressure force oriented towards the bottom opening and exerted directly onto the head presses the head against the retainer element. The pressure force is exerted directly onto the head by an element other than the retainer element (for example by the rod and/or the locking element). In other words, the head is locked between the rod and the retainer element, or between the locking element (as a pressure element) and the retainer element, or between all three of these elements.

In the state of final locking, the locking element continues to impede radial expansion of the retainer element and the retainer element is firmly held in position in the accommodation space of the receiving part by virtue of the engagement structure. In one non-limiting example embodiment, the engagement structure holding the retainer element is an annular groove formed in the accommodation space, allowing for expansion of the retainer element when the locking element is in the first position. The head of the anchoring element may be inserted into the opening of the accommodation space.

The retainer element is supported by the engagement structure in the accommodation space of the receiving part as well as by radial engagement of the locking element. Because the retainer element does not take part in exerting a pressure force from the rod or another element (such as a pressure element) onto the head, the function of the retainer element is limited to retaining the head of the anchoring element in the coupling assembly. Accordingly, the reliability and durability of the retainer element is enhanced.

Further, the retainer element does not need to fully encompass the head of the anchoring element, unlike in above described document U.S. Pat. No. 6,248,105 B1. As result, the size of the retainer element, particularly in the direction along the central axis of the receiving part (as seen when being held in position), is considerably reduced. As such, the retainer element may be loaded into the accommodation space from a top direction opposite the opening of the accommodation space. Hence, in situ assembly of the parts is improved and the width of the bottom opening may be narrowed to almost the diameter of the head. As a consequence, the stability, reliability and durability of the retainer element is further increased, and dimensions of the receiving part may be reduced.

BRIEF DESCRIPTION OF THE DRAWINGS

The invention will be better understood from the description of various embodiments taken in conjunction with the accompanying drawings. In the drawings:

FIG. 14 shows a perspective exploded view of a second embodiment of a polyaxial bone anchoring device;

FIG. 15 shows a perspective view of the bone anchoring device of FIG. 14 in an assembled state;

FIG. 16 shows a cross-sectional view of the bone anchoring device in an assembled state according to the second embodiment;

FIG. 17 shows a perspective view of a bone anchoring element employed in conjunction with the second embodiment;

DETAILED DESCRIPTION

Figure 1:
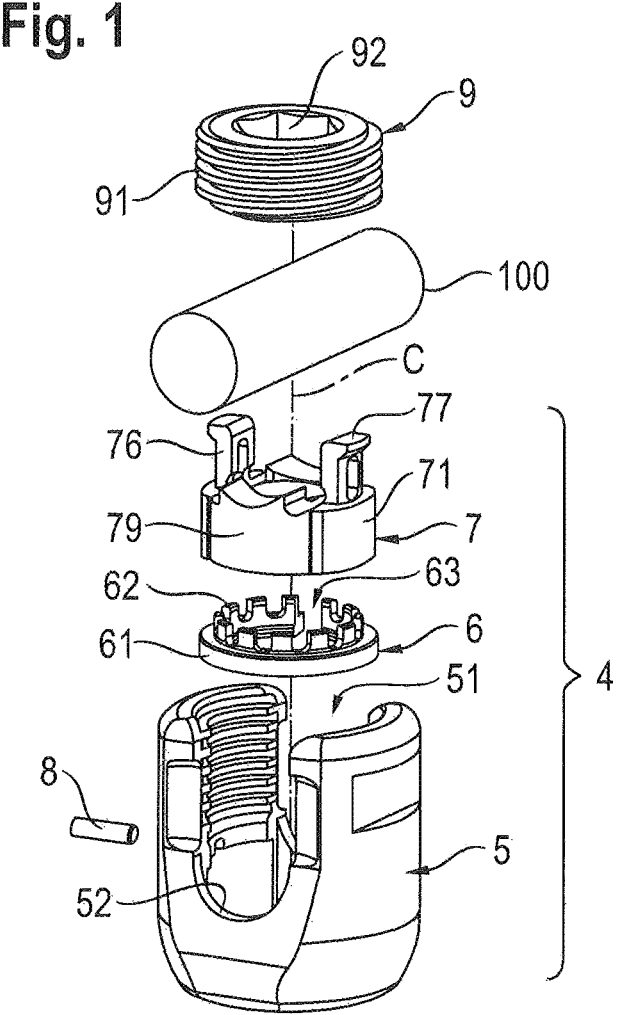
FIG. 1 shows a perspective exploded view of a first embodiment of a polyaxial bone anchoring device.
Figure 2:
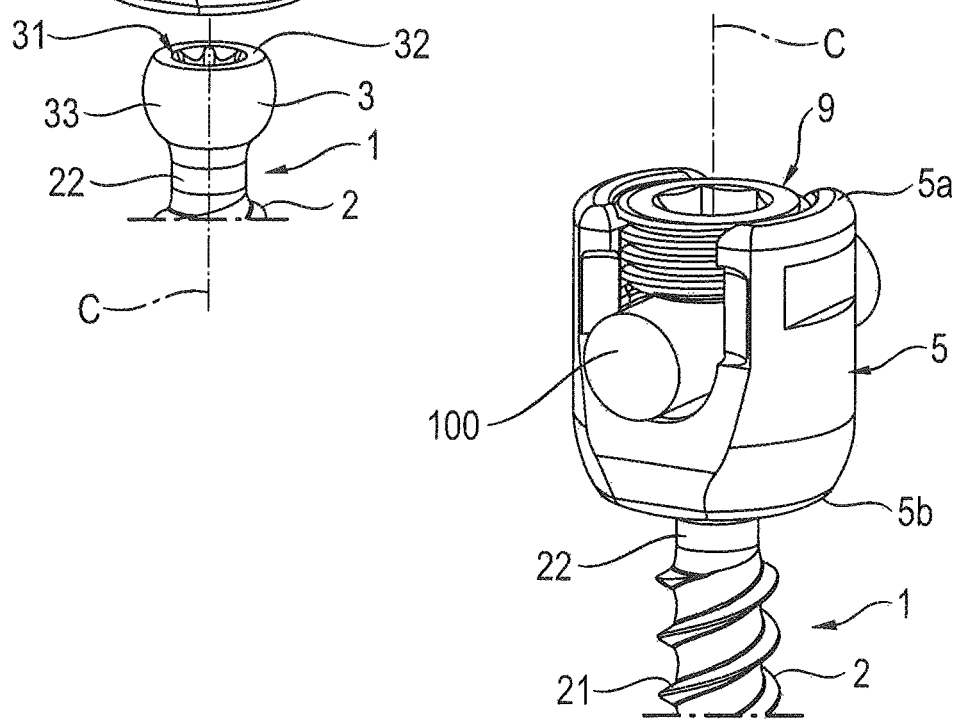
FIG. 2 shows a perspective view of the bone anchoring device of FIG. 1 in an assembled state.
Figure 3:
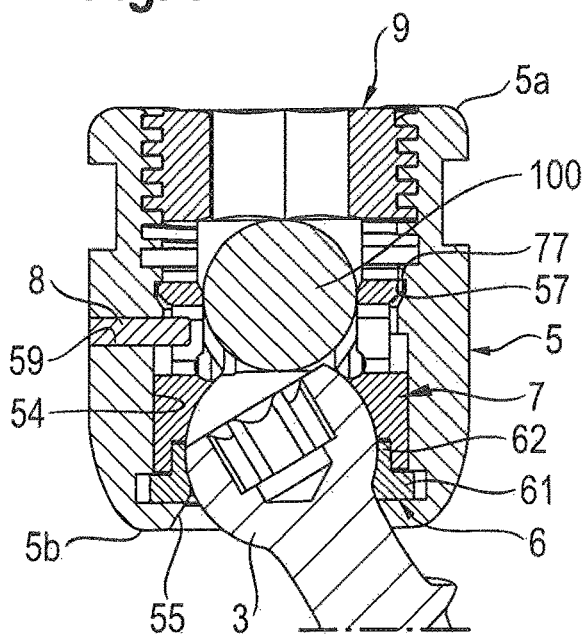
FIG. 3 shows a cross-sectional view of the bone anchoring device of FIGS. 1 and 2.

A first embodiment of a coupling assembly and a polyaxial bone anchoring device is explained with reference to FIGS. 1-13C. FIGS. 1-3 provide an overview of the assembly and device and FIGS. 4A-9B provide details of the assembly and device. FIGS. 10A-13C illustrate the use of the assembly and device according to the first embodiment.

As shown in FIG. 1, a polyaxial bone anchoring device includes an anchoring element 1, a coupling assembly 4, and a fixation element 9, such as a set screw, for connecting a rod 100 with the anchoring element 1. The anchoring element 1 has a spherically segment-shaped head 3 having a flat top portion 32, an engagement portion 31 for engagement by an external tool such as a driver, and a spherical portion 33. The anchoring element 1 further has a shank 2 provided with a bone thread 21 and a neck portion 22 connecting the shank 2 to the head 3.

Figure 4A:
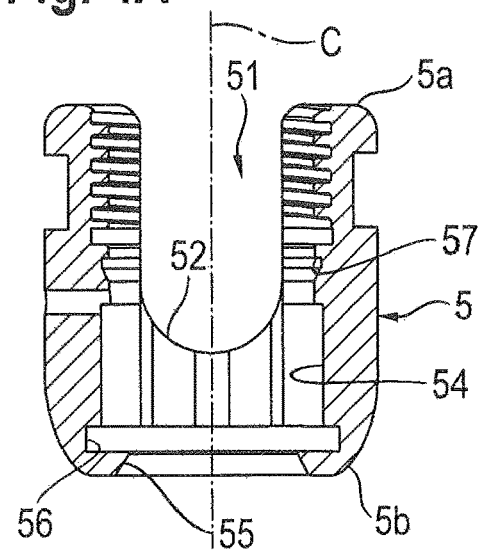
FIG. 4A shows a cross-sectional view of a receiving part according to the first embodiment, the cross-section taken along a line AA in FIG. 4B.
Figure 4B:
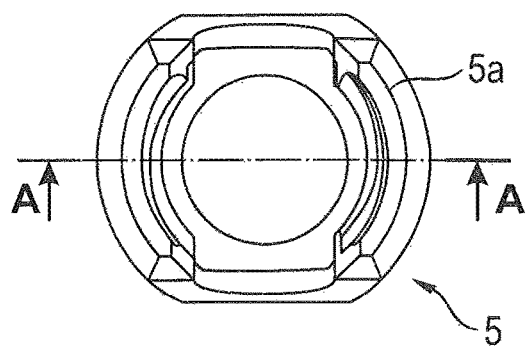
FIG. 4B shows a top view of the receiving part of FIG. 4A.

The coupling assembly 4 includes a receiving part 5, a retainer element 6, a locking element 7, and a pin 8. The receiving part 5 has a substantially cylindrical shape with optionally flat sides and engagement portions for engagement by an external tool. The receiving part 5 has a top end 5a, a bottom end 5b, and an inner bore 51 extending from the top end 5a in a direction towards the bottom end 5b as shown in FIG. 4A. As can be seen in more detail in FIGS. 3-5B, an opening 55 is formed at the bottom end 5b that permits introduction of a head 3 into an accommodation space 54. The accommodation space 54 extends from the opening 55 towards the bore 51 in the receiving part 5.

In this embodiment, the accommodation space 54 has a cylindrical shape and has an annularly extending groove at the bottom end of the accommodation space 54 adjacent to the opening 55. The annularly extending groove functions as an engagement structure 56 for the retainer element 6 and is arranged to receive an annularly shaped engagement portion of the retainer element 6, described below. The bore 51, the accommodation space 54, and the annular engagement structure 56 are symmetric and coaxial with respect to a central axis C of the receiving part 5.

Figure 5A:
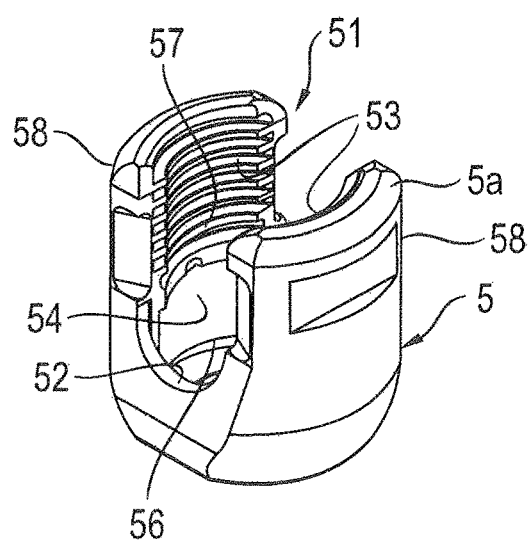
FIG. 5A shows a perspective view from above the receiving part shown in FIG. 4A.
Figure 5B:
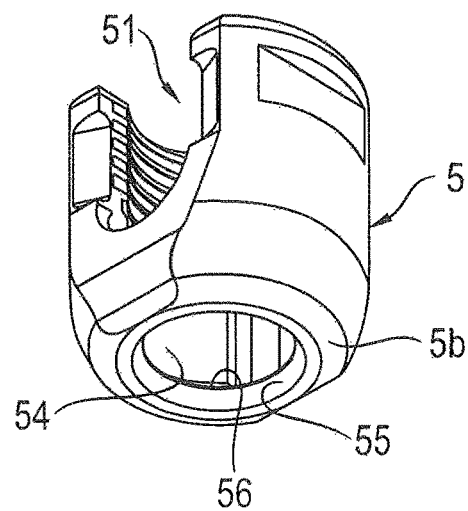
FIG. 5B shows a perspective view from below the receiving part shown in FIG. 4A.
Figure 6A:
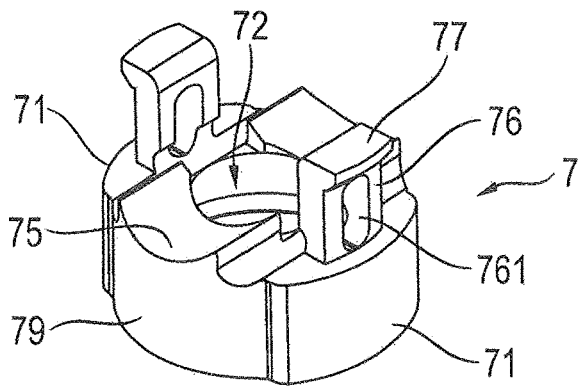
FIG. 6A shows a perspective view from above a locking element according to the first embodiment.
Figure 6B:
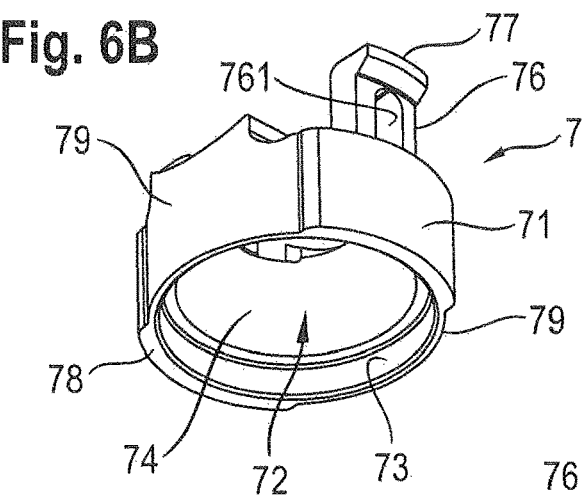
FIG. 6B shows a perspective view from below the locking element of FIG. 6A.
Figure 7A:
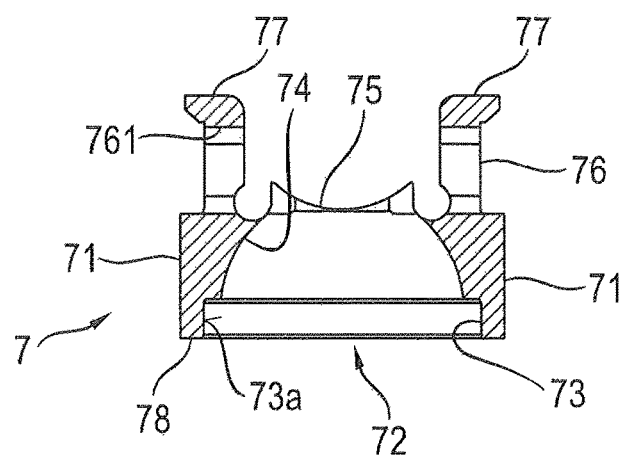
FIG. 7A shows a cross-sectional view of the locking element shown in FIG. 6A, the cross-section taken along a line BB in FIG. 7B.
Figure 7B:
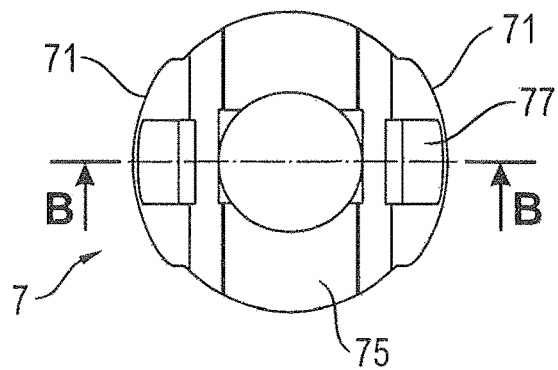
FIG. 7B shows a top view of the locking element of FIG. 6A.
Figure 8A:
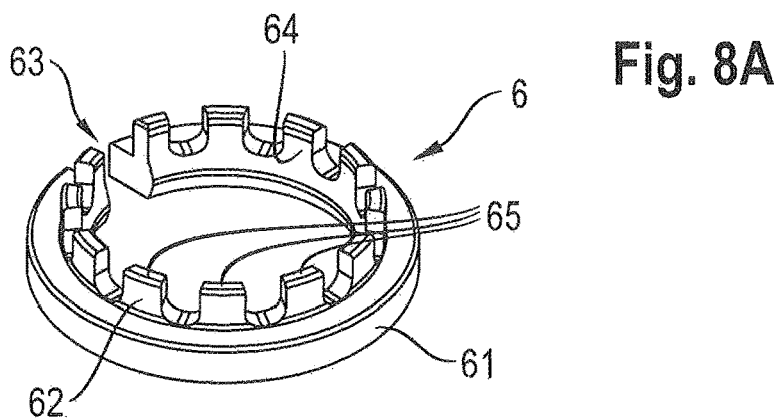
FIG. 8A shows a perspective view from above a retainer element according to the first embodiment.
Figure 8B:
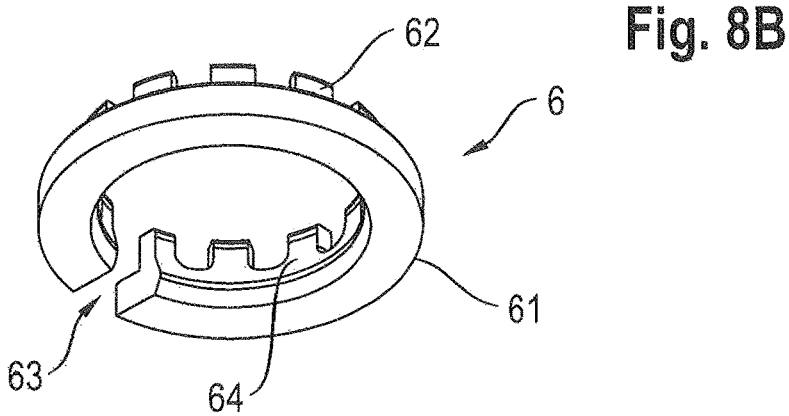
FIG. 8B shows a perspective view from below the retainer element of FIG. 8A.

As shown in FIGS. 1, 4A, and 5A, a U-shaped recess 52 extends from the top end 5a of the receiving part 5 defining two free legs 58. Threads 53 are provided at an inner side of the legs 58 facing the inner bore 51. A fixation element 9 is provided having an engagement portion 92 for an external tool such as a driver (not shown) and an external thread 91 to be threaded into the threads 53 of the receiving part 5. The fixation element 9 will tighten, fixate and lock a rod 100 in the recess 52 of the receiving part 5, as well as the head 3 of the anchoring element 1 when inserted into the accommodation space 54.

The locking element 7 is explained in more detail with reference to FIGS. 6A-7B. The locking element 7 has two outer cylindrical surface portions 71 arranged opposite with respect to each other. Both cylindrical surface portions 71 define an outer diameter of the locking element 7 substantially corresponding to an inner diameter of the accommodation space 54 of the receiving part 5. Consequently, when the locking element 7 is provided in the accommodation space 54, the locking element 7 is in sliding engagement with the inner walls of the accommodation space 54 and is translationally movable along the central axis C. Further, a circumference of locking element 7 includes two opposite recessed outer cylindrical surface portions 79 having a reduced diameter relative to the outer cylindrical surface portions 71. The recessed outer cylindrical surface portions 79 are located transverse to the cylindrical surface portions 71. Both recessed outer cylindrical surface portions 79 extend respectively between the outer cylindrical surface portions 71. The reduced diameter of the recessed outer cylindrical surface portions 79 is selected to be less than an inner diameter of the inner bore 51, and may be less than an inner diameter of the threads 53, to allow introduction of the locking element 7 into the receiving part 5 from the top end 5a in a posture rotated by 90 degrees as compared with the finally assembled state, as shown, for example, in FIGS. 11A-C.

The locking element 7 further has on its top face a rod-receiving portion 75, which is arranged to receive the rod 100 as shown in FIGS. 1 and 2. Further, an inner coaxial bore provides access to an inner cavity 72 of the locking element 7, which has a spherical segment-shaped recess 74 in an upper portion for receiving the partially spherical head 3 and a recess 73 in a bottom portion having a substantially cylindrical inner wall 73a. Inner wall 73a may also have a conical or otherwise tapered shape. The recess 73 is adapted to receive a corresponding cylindrical, conical or tapered, etc. engagement portion 62 ("second engagement portion") of the retainer element 6 to be described below.

Figure 13A:
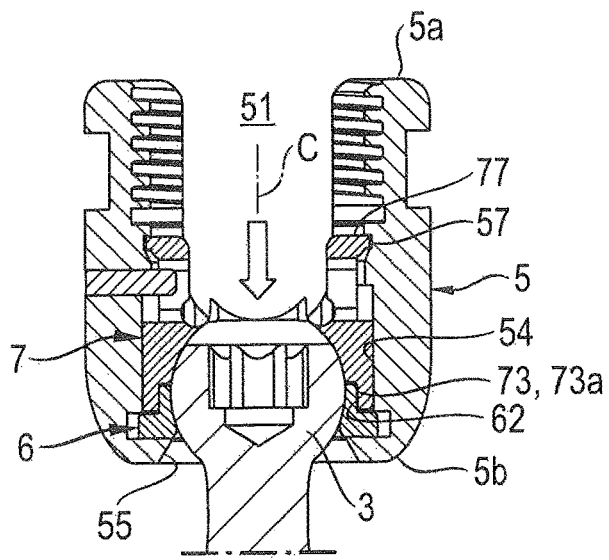
FIG. 13A shows a step of locking the retainer element and simultaneously pre-locking the head of the anchoring element with a friction-fit according to the first embodiment.

The spherical segment-shaped recess 74 of the locking element 7 is sized and adapted to the spherical portion 33 of the head 3 to allow selecting a specific polyaxial orientation (e.g., an angular orientation) of the anchoring element 1 relative to the receiving part 5 in a pre-locked state or in a finally locked state, described below. To establish a pre-locked state in this embodiment, two arms 76 are provided in a top portion of the locking element 7. The ends of the arms 76 are provided with engagement shoulders 77. As shown in FIGS. 3 and 13A, the engagement shoulders 77 may resiliently engage with corresponding engagement shoulders 57 of the receiving part 5, which are provided in a wall portion of the inner bore 51, for example, near the bottom end of the threads 53. The length of the arms 76 of the locking element 7 and the vertical positions of the engagement shoulders 57 at the inner wall of the bore 51 of the receiving part 5 are selected such that when the shoulders 57, 77 snap-in and mutually engage with each other, the second engagement portion 62 of the retainer element 6 is at least partially received in the recess 73 having the inner wall 73a as shown in FIG. 13A. In such a state, the retainer element 6 is locked and the head 3 is prevented from being released from the retainer element 6, which is denoted herein as a pre-locked state.

As can be seen from FIGS. 3 and 13A-C, when the rod 100 is received by the rod-receiving portion 75 of locking element 7, exertion of a pressure force on the rod 100 by a fixation element 9 will lead to a transfer of the pressure force onto the locking element 7. The locking element 7 transfers the pressure force via its inner spherical segment-shaped recess 74 onto the head 3 of anchoring element 1. As such, the locking element 7 of the first embodiment functions as a pressure element.

Details of the retainer element 6 are explained with reference to FIGS. 8A-9B. The retainer element 6 is substantially ring-shaped with a slit 63. The retainer element 6 thus represents an open ring. The slit 63 allows the retainer element 6 to be radially expanded and/or compressed. The retainer element 6 includes a ("first") substantially annular engagement portion 61 configured to be received by the annular engagement groove of the engagement structure 56 of the receiving part 5, provided at the accommodation space 54 as shown in FIG. 10D. The retainer element 6 also includes the second engagement portion 62, which in this embodiment has a slightly conical outer appearance, but may also be cylindrical or otherwise tapered. The second engagement portion 62 has a plurality of regularly arranged flanges or lugs 65 separated by U-shaped slots to yield a crown-like arrangement. The invention is not limited to the specific arrangement shown herein. Other kinds of projections are possible or a single conical, cylindrical, rounded or tapered wall is possible as well. As shown in FIG. 13A, the second engagement portion 62 is configured to be received by the recess 73 of locking element 7, which may have a cylindrical, conical, tapered or rounded inner wall 73a. Once received in the recess 73 of locking element 7, the second engagement portion 62 is prevented from further expansion by abutting against the inner wall 73a. In this embodiment, the second engagement portion 62 extends from the first engagement portion 61 towards the top end 5a of the receiving part 5, when being inserted therein. The first and second engagement portions 61, 62 are formed as a monolithic, single piece.

Figure 9A:
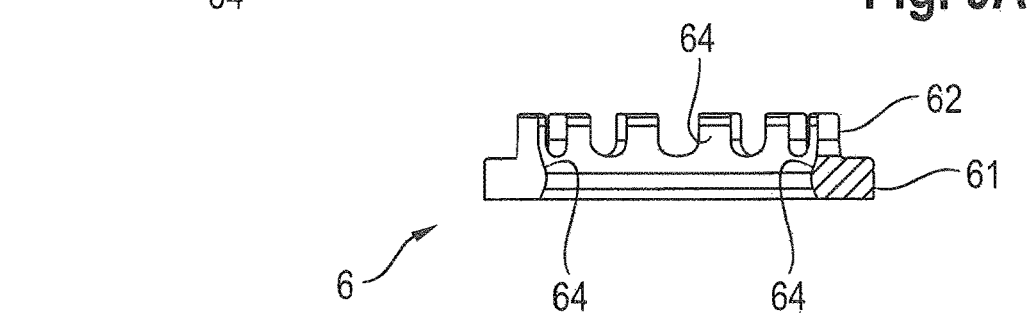
FIG. 9A shows a cross-sectional view of the retainer element of FIG. 8A, the cross-section taken along line DD in FIG. 9B.
Figure 9B:
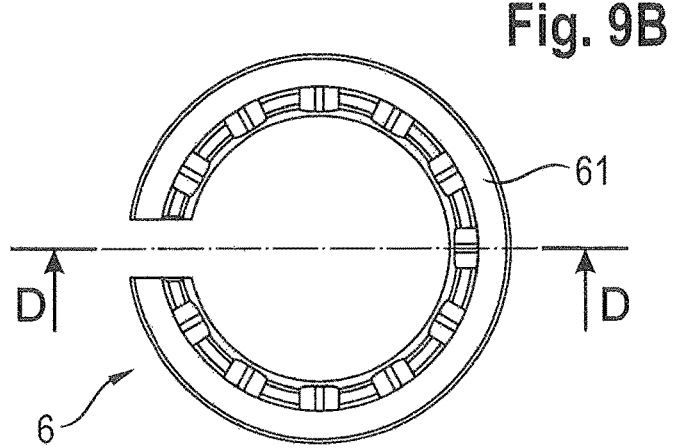
FIG. 9B shows a top view of the retainer element of FIG. 8A.

While the outer appearance of the second engagement portion 62 may be cylindrical, conical, tapered or rounded etc., an inner wall of the retainer element 6 includes a hollow spherical segment-shaped portion 64 as can particularly be seen in FIG. 9A. A curvature of the spherical segment-shaped portion 64 corresponds to that of spherical portion 33 of head 3 of anchoring element 1. In other words, spherical segment-shaped portion 64 is arranged to receive and retain the head 3 of anchoring element 1.

When the second engagement portion 62 of the retainer element 5 is received in the recess 73 of the locking element 7, a locked state of the retainer element 6 retains the head 3 of anchoring element 1. In such a state, the inner diameter of the retainer element 6 is less than that of the head 3 to prevent release of the head 3 from retainer element 6 (which may also be a compressed state of the retainer element 6).

The assembly and use of the coupling assembly 4 according to the first embodiment is explained with reference to FIGS. 10A-13C.

Figure 10A:
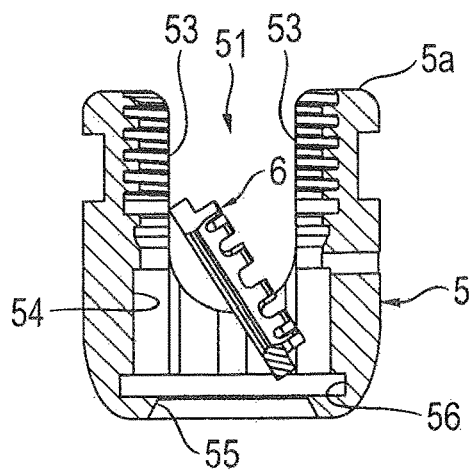
FIG. 10A shows a cross-sectional view of a first step of inserting a retainer element into a receiving part according to the first embodiment.
Figure 10B:
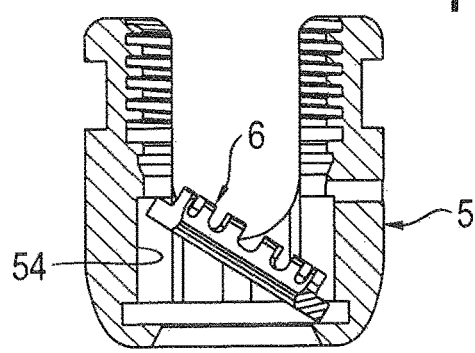
FIG. 10B shows a cross-sectional view of a second step of inserting the retainer element into the receiving part according to the first embodiment.
Figure 10C:
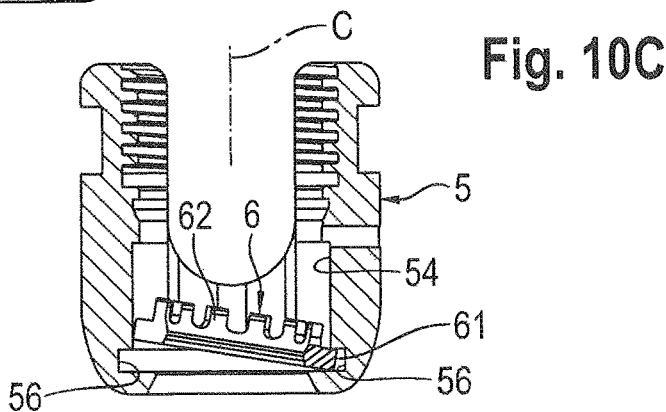
FIG. 10C shows a cross-sectional view of a third step of inserting the retainer element into the receiving part according to the first embodiment.
Figure 10D:
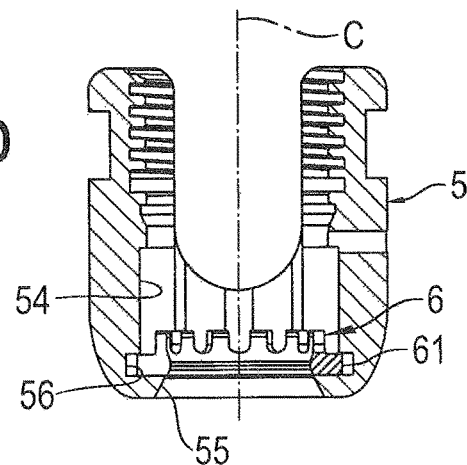
FIG. 10D shows a cross-sectional view of a state in which the retainer element is held in position by an engagement structure of the receiving part according to the first embodiment.

The insertion of the retainer element 6 into the receiving part 5 is explained with reference to FIGS. 10A-10D. As can be seen in FIG. 10A, the retainer element 6 is inserted into the bore 51 of the receiving part 5 from a top end 5a of the receiving part 5. Since an outer diameter of the retainer element 6 is larger than an inner diameter of the bore 51, in particular of the inner threads 53, the retainer element 6 is inserted in an inclined or tilted angle relative to the annular engagement structure 56 of the receiving part 5. The retainer element 6 is then rotated or tilted towards a horizontal posture when the retainer element 6 reaches its predetermined position in the accommodation space 54. As can be seen in FIGS. 10B and 10C, once the retainer element 6 has reached the accommodation space 54 having a larger inner diameter as compared with the bore 51, the retainer element 6 can be brought into a position less inclined and closer to a coaxial orientation with respect to central axis C.

In an unstressed, unbiased state of the retainer element 6, an outer diameter of the annular engagement portion 61 is larger than an inner diameter of the accommodation space 54 such that the retainer element 6 abuts an inner wall of the accommodation space 54 when the retainer element 6 is inserted into the accommodation space 54. The outer diameter of the retainer element 6 is selected to permit the retainer element 6 to be held in a coaxial position with the central axis C when the annular engagement portion 61 of the retainer element 6 enters and snaps into the annular engagement groove of the engagement structure 56 of the receiving part 5, as depicted in FIG. 10D. The retainer element 6 is slightly compressed from the unstressed state until it snaps into the groove of the engagement structure 56, where the retainer element 6 expands again into the unstressed state. The groove of the engagement structure 56 has a larger inner diameter than the outer diameter of the annular engagement portion 61 of the retainer element 6 in the unstressed state. The diameter of the groove of the engagement structure 56 provides enough tolerance, or play, to allow expansion of the retainer element 6 from the unstressed state when the head 3 of anchoring element 1 is inserted, as described below.

Figure 11A:
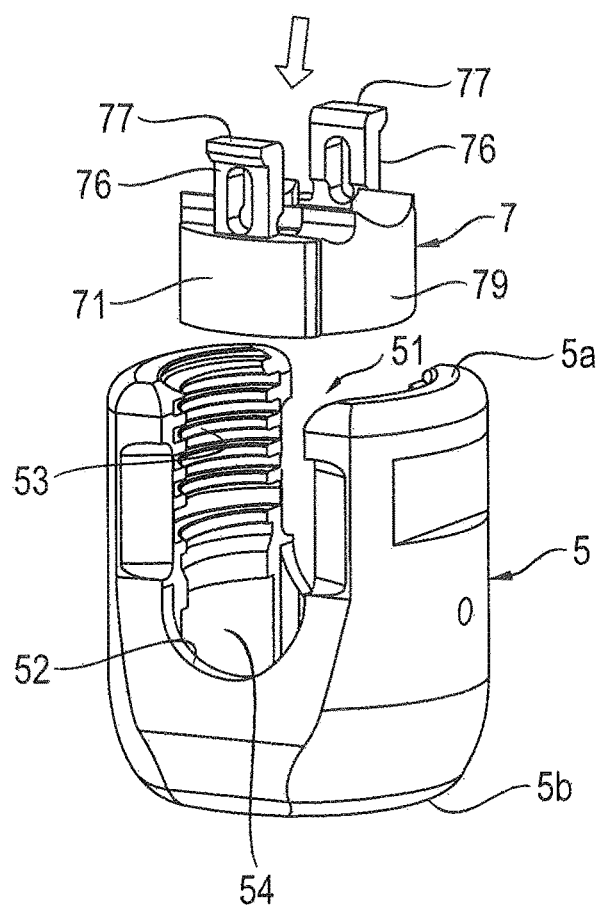
FIG. 11A shows a perspective view of a first step of inserting a locking element into the receiving part according to the first embodiment.

Insertion of the locking element 7 into the receiving part 5 is explained with reference to FIGS. 11A-11C. As shown in FIG. 11A, the locking element 7 is introduced into the bore 51 of the receiving part 5 from the top end 5a. Thereby, the protruding outer cylindrical surface portions 71 of the locking element 7 face towards the U-shaped recesses 52 of the receiving part 5, i.e., the orientation of the locking element 7 with respect to its final installed state is offset by 90 degrees. Further, the recessed outer cylindrical surface portions 79 of the locking element 7 face the threads 53 of the receiving part 5 to allow safe passage of the locking element 7 within bore 51 and past threads 53.

Figure 11B:
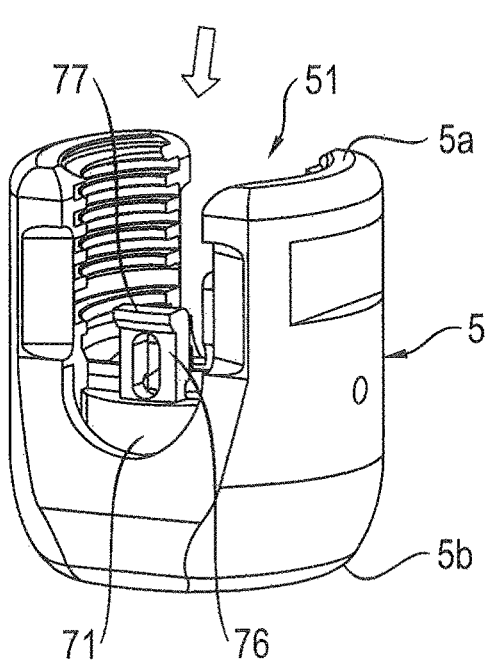
FIG. 11B shows a perspective view of a second step of inserting the locking element into the receiving part according to the first embodiment.

As shown in FIG. 11B, when the locking element 7 (more specifically, its bottom or base portion including outer cylindrical surface portions 71, 79) has passed the inner threads 53 and reached the accommodation space 54 of the receiving part 5, the locking element 7 may be rotated by 90 degrees by sliding engagement between the outer cylindrical surface portions 71 with the inner wall portions of the accommodation space 54.

Figure 11C:
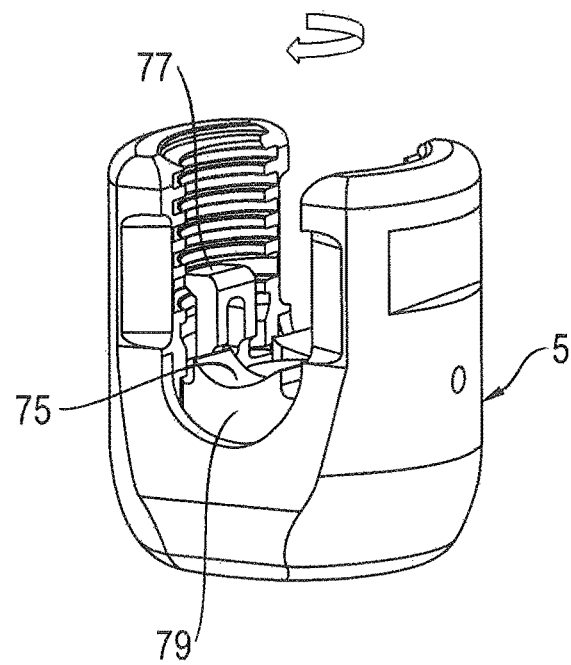
FIG. 11C shows a perspective view of a third step of inserting the locking element into the receiving part according to the first embodiment.

As shown in FIG. 11C, the locking element 7 is then rotated by 90 degrees into its final position with the arms 76 and shoulders 77 oriented towards the legs 58 having the threads 53 and engagement shoulders 57, to prepare for engagement of engagement shoulders 57 and 77 to establish the pre-locked state explained below with respect to FIG. 13A. In the state shown in FIG. 12A, the protrusions of the arms 76, which bear the shoulders 77, rest upon corresponding protrusions at the inner wall of the bore 51 of the receiving part 5. The bore 51 provides the engagement shoulders 57, which face down towards the opening 55 and bottom end 5b (see FIGS. 3 and 4A). In other words, shoulders 57, 77 are not yet engaged.

Figure 12A:
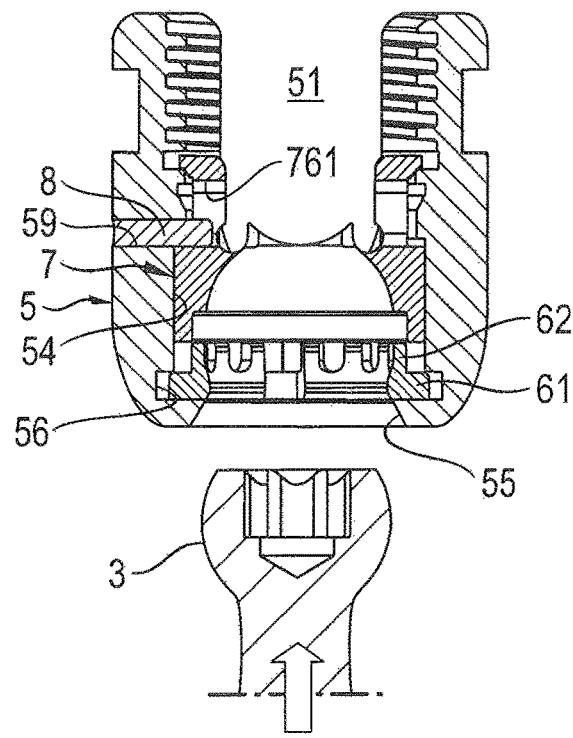
FIG. 12A shows a cross-sectional view of a state of the coupling assembly wherein the locking element is in a first position according to the first embodiment.

FIGS. 12A-12D depict the process of inserting the head 3 of the anchoring element 1 in the accommodation space 54 of the receiving part 5. As shown in FIG. 12A, prior to insertion of the head 3, a pin 8 is inserted into an elongate hole 59 formed in a side wall of the receiving part 5. A tip portion of the pin 8 protrudes into the bore 51 of the receiving part 5 and into an elongated aperture 761 formed in the arms 76 of the locking element 7. In this state, the locking element 7 is prevented from unintended rotation back into the position in which the locking element 7 was inserted into the receiving part 5 (i.e., a 90 degree rotation).

Figure 12B:
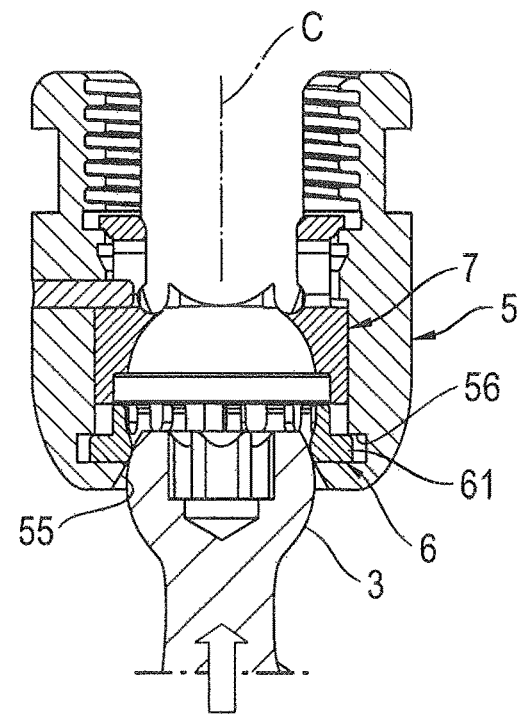
FIG. 12B shows a cross-sectional view of a state of the coupling assembly wherein a head of an anchoring element is inserted into an opening of coupling assembly according to the first embodiment.
Figure 12C:
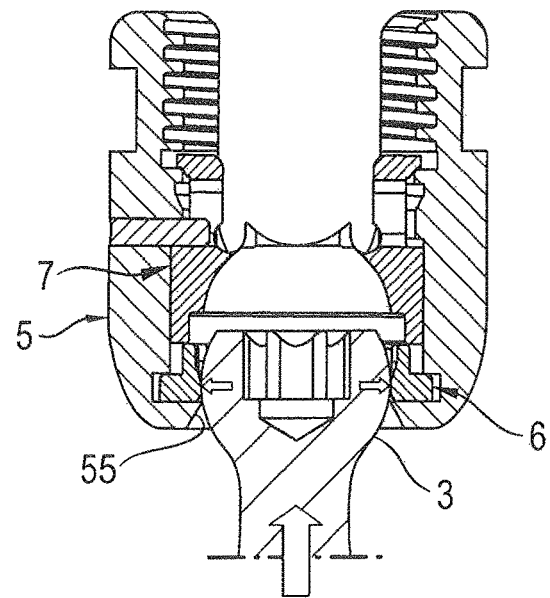
FIG. 12C shows a cross-sectional view of a state of the coupling assembly wherein the retainer element is expanded by the head of an anchoring element according to the first embodiment.

Next, as shown in FIG. 12B, the head 3 of the anchoring element 1 is introduced into the opening 55 whereby the spherical portion 33 of the head 3 contacts an inner wall of the retainer element 6. Since the flange-like first engagement portion 61 of the retainer element 6 is firmly received in the engagement groove of the engagement structure 56 of the receiving part 5, the retainer element 6 is held in a coaxial position with the central axis C. In this position, no translation along the central axis C is possible, and the retainer element 6 starts to expand in a radial direction responsive to further insertion of the head 3, which locally increases in diameter as shown by the arrows in FIG. 12C. The radial play or tolerance in the engagement structure 56 relative to the outer diameter of the retainer element 6 in the unstressed state is thereby the same as or even larger than a difference between the maximum outer diameter of head 3 and the minimum inner diameter of retainer element 6 in the unstressed state, i.e., equal to or larger than the amount of expansion.

Figure 12D:
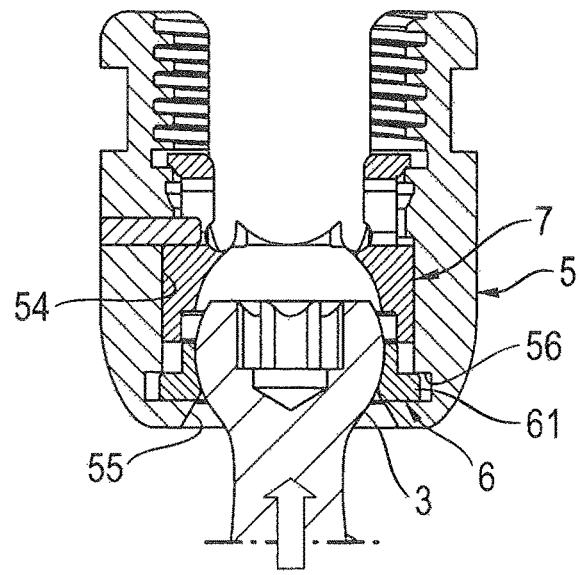
FIG. 12D shows a cross-sectional view of a state of the coupling assembly wherein insertion of the head of the bone anchoring element is completed, the head is received by a hollow spherical segment-shaped recess portion of the retainer element and the locking element continues to be in the first position, according to the first embodiment.

As shown in FIG. 12D, further insertion of the head 3 allows the retainer element 6 to return into an unstressed or at least a less expanded state. The retainer element 6 along with the receiving part 5 snaps onto the head 3 by virtue of the compressive force of the retainer element 6. FIG. 12D shows that the locking element 7 is still in an unlocked "first" position with respect to the retainer element 6. Nevertheless, since in this state, the spherical head 3 is now received and mated with the inner spherical segment-shaped surface 64 of the retainer element 6, a sufficient amount of friction is generated therebetween to maintain an angular orientation of the anchoring element 1 as desired with respect to the receiving part 5 during assembly and during in-situ applications prior to final locking. As a consequence, a friction-fit connection between the head 3 and the retainer element 6 is achieved.

Steps of pre-locking and final locking of the head 3 of the anchoring element 1 as well as locking of the retainer element 6 is explained with reference to FIGS. 13A-13C. As shown in FIG. 13A, locking of the retainer element 6 and pre-locking of the head 3 of the anchoring element 1 is accomplished by moving the locking element 7 from the first position (shown in FIG. 12D) to a second position. In the second position, the second engagement portion 62 of the retainer element 6 is received in recess 73 and/or cavity 72 of the locking element 7 such that an outer surface of the second engagement portion 62 is radially engaged from the outside by the inner wall 73a, and the retainer element 6 is hindered from further expansion. However, some play between the inner wall 73a and the second engagement portion 62 is permitted as long as the head 3 is prevented from being released. In this state, the retainer element 6 is locked and the head 3 cannot be released from the accommodation space 54 or from the opening 55.

Figure 13B:
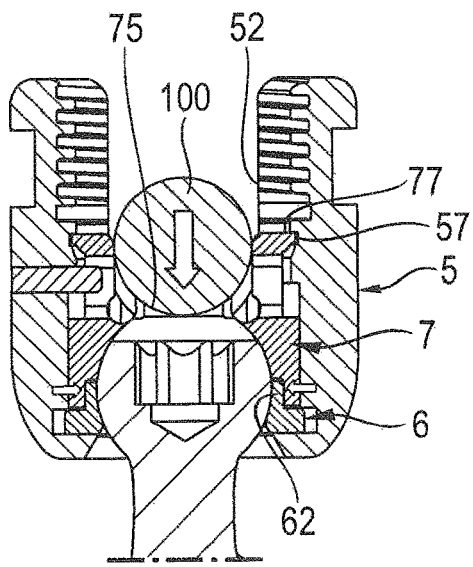
FIG. 13B shows a step of inserting a rod into the polyaxial bone anchoring device according to the first embodiment.

In a next step shown in FIG. 13B, the rod 100 is inserted into the U-shaped recess 52 and received by the rod receiving surface 75 of the locking element 7. A compressive force exerted by the locking element 7 onto the second engagement portion 62 of the retainer element 6 is generated when forces trying to remove the anchoring element 1 out of the opening 55 are generated.

FIGS. 13A and 13B also show a pre-locked state of the head 3 in the receiving part 5. In conjunction with the locking of the retainer element 6 due to the sliding movement of the locking element 7 towards the opening 55 and bottom end 5b along the central axis C, the arms 76 of the locking element 7 flex inwards and the shoulders 77 provided at the tips of arms 76 of the locking element 7 latch resiliently into corresponding recesses providing the shoulders 57 at the inner wall of the inner bore 51 of the receiving part 5. In this state, see FIG. 13A, the retainer element 6 is prevented from expanding beyond the inner walls 73a such that the head 3 cannot be released any more from the retainer element 6 ("pre-lock"). At the same time, the above described friction-fit connection between the head 3 and the retainer element 6 is maintained.

Figure 13C:
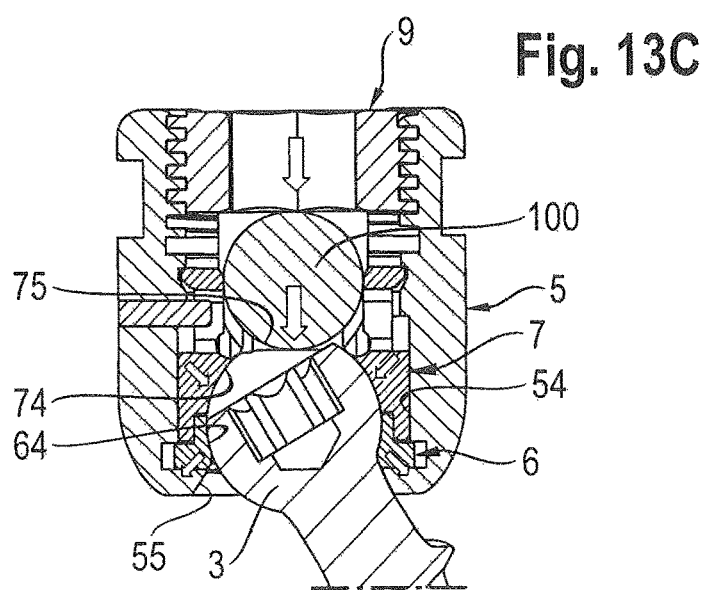
FIG. 13C shows a step of tightening a fixation element and final locking of the head of the anchoring element at a selected orientation with pressure forces exerted, according to the first embodiment.
Figure 18A:
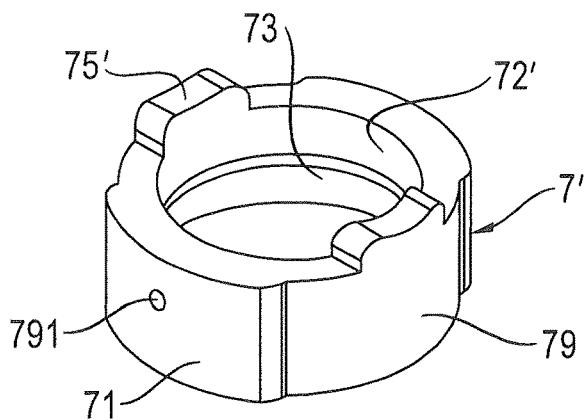
FIG. 18A shows a perspective view from above the locking element of FIG. 14 according to the second embodiment.
Figure 18B:
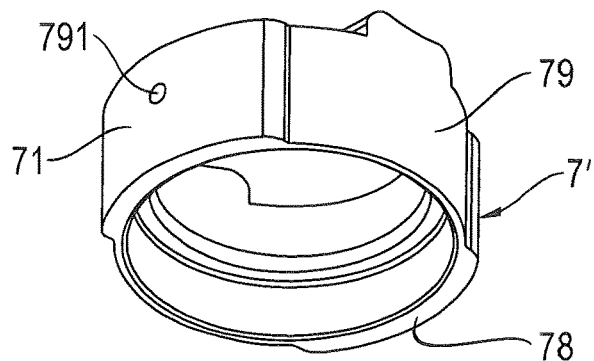
FIG. 18B shows a perspective view from below the locking element of FIG. 18A.
Figure 19A:
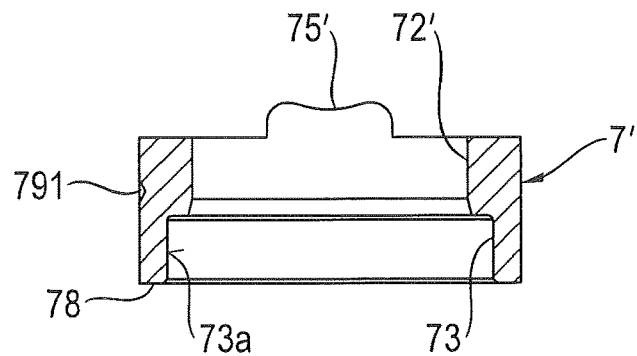
FIG. 19A shows a cross-sectional view of the locking element of FIG. 18A, the cross-section taken along a line EE in FIG. 19B.
Figure 19B:
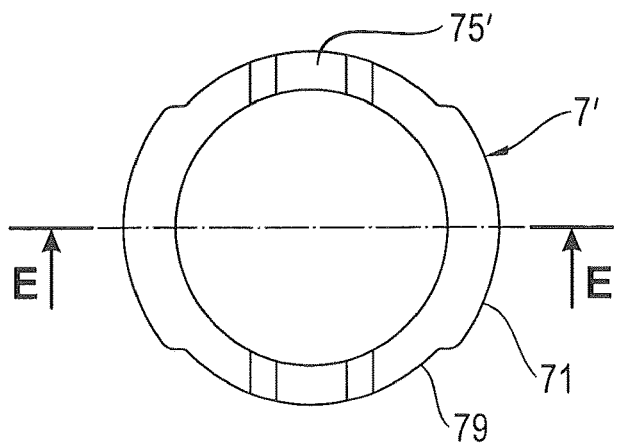
FIG. 19B shows a top view of the locking element of FIG. 18A.

FIG. 13C shows the steps of final locking of the head 3 in the receiving part 5. The fixation element 9 is screwed into the thread 53 of the receiving part 5 and exerts a downward pressure force onto the rod 100. The rod 100 transfers this pressure force onto the rod receiving portion 75 of the locking element 7, which exerts a pressure force on the head 3 thereby pressing the head 3 against the hollow spherical segment-shaped portion 64 of the retainer element 6. The retainer element 6 cannot expand because the retainer element 6 is locked by the locking element 7. The retainer element 6 also cannot slide down towards the opening 55 and bottom end 5b because the engagement portion 61 is received in the engagement structure 56. The direction of pressure forces exerted are indicated by arrows in FIG. 13C.

Because the retainer element 6 is dimensioned and shaped to allow insertion into the receiving part 5 from the top end 5a as shown in FIGS. 10A-10D, the bottom opening 55 of the receiving part 5 may have a smaller diameter than the retainer element 6, which further supports the retainer element 6 in the engagement structure 56 adjacent the opening 55. The further support of the retainer element 6 is made possible by exerting pressure forces directly onto the head 3 via the locking element 7 instead of the retainer element 6, as would be suggested by the spring chuck in above described document U.S. Pat. No. 6,248,105 B1. As compared with the spring chuck, the retainer element 6 is limited in function to retaining the head 3. As such, the dimensions of the retainer element 6 along the central axis C (i.e., the height of the retainer element 6) may be selected to be shorter allowing introduction of the retainer element 6 into the receiving part 5 from the top end 5a, which permits selecting a smaller width for the bottom opening 55.

A second embodiment of the present invention is explained with respect to FIGS. 14-20D. Like parts as in the first embodiment are referenced with the same numerals, and description thereof will not be repeated herein. The second embodiment differs from the first embodiment mainly with regard to the locking element 7' and the anchoring element 1', and to some extent with respect to the receiving part 5'. More specifically, the second embodiment does not provide for a pre-locked state, and the locking element 7' is not arranged as a pressure element. However, features of the retainer element 6 and the interaction with the locking element 7' as well as with the engagement structure are the same between both embodiments.

As shown in FIGS. 14-16, the coupling assembly 4' includes a receiving part 5', the retainer element 6, and a locking element 7'. The receiving part 5' differs from the receiving part 5 of the first embodiment in that bore hole 59 is not provided. A bore hole 59 would allow introducing a pin 8 to lock the locking element 7' in a pre-lock position. Instead, a crimp bore 591 is formed in a side wall of the receiving part 5'.

The locking element 7' of the second embodiment differs from the locking element 7 of the first embodiment in that arms 76 or shoulders 77 are not provided, which in the first embodiment, facilitate a pre-locked state with a friction-fit between the locking element 7 (pressure element) and the head 3. Instead, the locking element 7' of the second embodiment solely serves to lock the retainer element 6 to prevent release of the head 3' from the receiving part 5'. As shown in FIGS. 18A-19B, a small recess 791 is formed in the protruding outer cylindrical surface 71 of the locking element 7'. The recess 791 is configured to receive a deformable portion at the end wall of the crimp bore 591 when the deformable portion is deformed to project into the accommodation space 54 of the receiving part 5' using an external tool (not shown).

As shown in FIGS. 18A-19B, the locking element 7' has a substantially cylindrical shape with protruding outer cylindrical surface portions 71 and outer recessed cylindrical surface portions 79 as in the first embodiment. However, locking element 7' does not have an inner spherical segment-shaped recess. Instead, the locking element 7' has an inner bore 72' allowing access to an engagement portion 31' of anchoring element 1' (see FIG. 17). The locking element 7' also has the recess 73 having inner wall 73*a* as in the first embodiment, which functions to engage the second engagement portion 62 of the retainer element 6 to lock expansion of the retainer element 6. The recess 73 is dimensioned and shaped similar to the first embodiment.

The locking element 7' of the second embodiment does not interact with the head 3' of anchoring element 1. Instead, as shown in FIG. 16, the rod 100 directly exerts a pressure force onto the head 3' of the anchoring element 1'.

The anchoring element 1' according to the second embodiment is shown in FIG. 17. The bone anchoring element 1' includes a spherical head 3' that has a spherical outer surface, including at the free upper end. The head 3' is wholly spherical. An engagement portion 31' provided at the free end includes wings 34 that extend in a spiral-like manner from a center point of the upper free end. In this embodiment, the engagement portion has four wings 34. The four wings 34 describe an outer contour of a cross with arms bent in the same direction. As such, the engagement surface of a driver is enhanced compared to usual polygon or other recesses, allowing for higher loads to be transferred to the head 3' by an external driver. Engagement portions for drivers and corresponding tools with a similar shape are known under the trademark Mortorq®. Due to the spherical contour of the head 3', the head 3' may extend through the recess 73 and the inner bore 72' such that a direct pressure transfer between the rod 100 and the head 3' can be established.

Assembly and use of the coupling assembly 4' and polyaxial bone anchoring device including the same according to the second embodiment is explained with respect to FIGS. 20A-D.

Figure 20A:
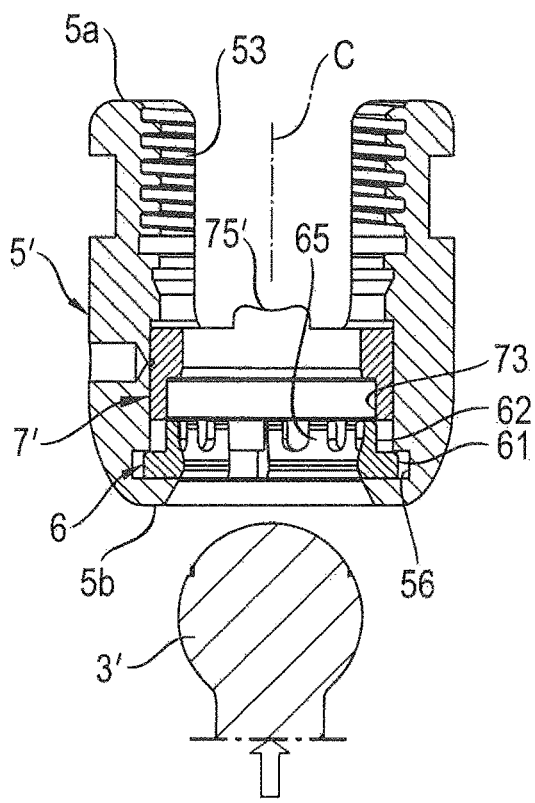
FIG. 20A shows a cross-sectional view of a state of the coupling assembly wherein the locking element is in a first position according to the second embodiment.

As shown in FIG. 20A, which corresponds to the state depicted in FIG. 12A regarding the first embodiment, prior to insertion of the head 3', the locking element 7' is introduced into the bore 71 of the receiving part 5' in a similar manner as shown in FIGS. 11A-C. Thereby, the rod receiving surface 75' is aligned with the rod receiving channel or U-shaped recess 52 of the receiving part 5'. The retainer element 6 is held in position by the groove of the engagement structure 56, which received the first engagement portion 61 of the retainer element 6.

Figure 20B:
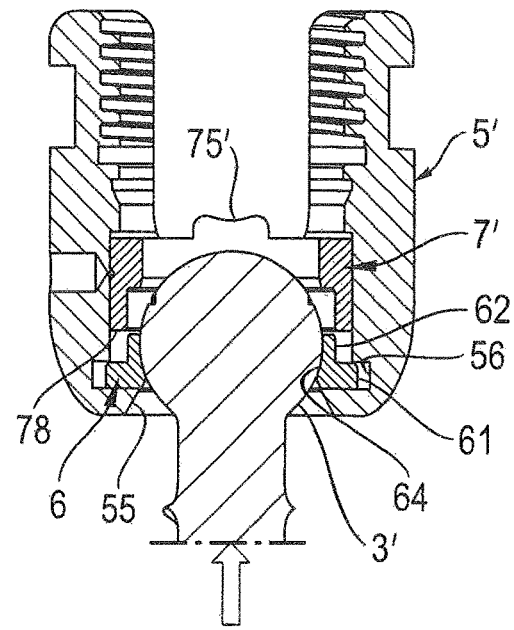
FIG. 20B shows a cross-sectional view of a state of the coupling assembly wherein insertion of the head of the bone anchoring element is completed, the head is received by a hollow spherical segment-shaped recess portion of the retainer element, and the locking element continues to be in the first position, according to the second embodiment.

Next, as shown in FIG. 20B, which corresponds to the state depicted in FIG. 12D with regard to the first embodiment, the head 3' has been inserted into the bottom opening 55 of receiving part 5' and received by the inner hollow spherical segment-shaped portion 64 of the retainer element 6. In FIGS. 20A and 20B, the locking element 7' is in the first unlocked position. The locking element 7' may be held in this temporary position by deforming a deformable portion at an end wall of crimp bore 591. The deformable portion then projects from an inner wall of the accommodation space 54 and into small recess 791 of locking element 7'.

Figure 20C:
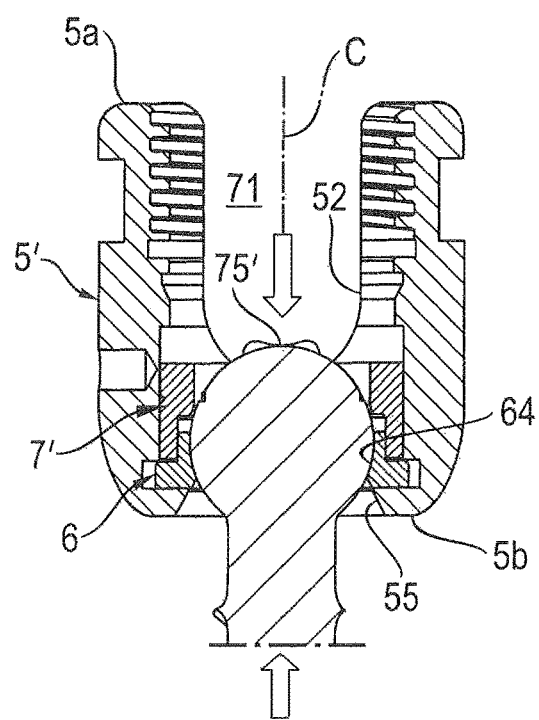
FIG. 20C shows a state in which the retainer element is locked by the locking element to retain the head within the accommodation space according to the second embodiment.

As shown in FIG. 20C, which corresponds to the state depicted in FIG. 13A with regard to the first embodiment, the locking element 7' is moved along the central axis C in sliding engagement between the cylindrical surface portions 71 and an inner wall of the accommodation space 54 towards the opening 55 and the bottom end 5*b*. The inner wall 73*a* of the cavity 73 is guided onto the second engagement portion 62 of the retainer element 6 to lock the retainer element 6. The comparatively small force exerted to move the locking element 7' may be achieved manually, e.g., by a tool, or by inserting the rod 100 with a small pressure force. As in the first embodiment, the locking element 7' hinders further expansion of the retainer element 6 when the second engagement portion 62 abuts against the inner wall 73*a* of the locking element 7'.

Because the locking element 7' does not have a spherical segment-shaped recess, the inner bore 72' may be shaped such that there is no or almost no contact between the locking element 7' and the head 3' of the anchoring element 1' when the head 3' is received in the hollow spherical segment-shaped recess 64 of the retainer element 6.

Figure 20D:
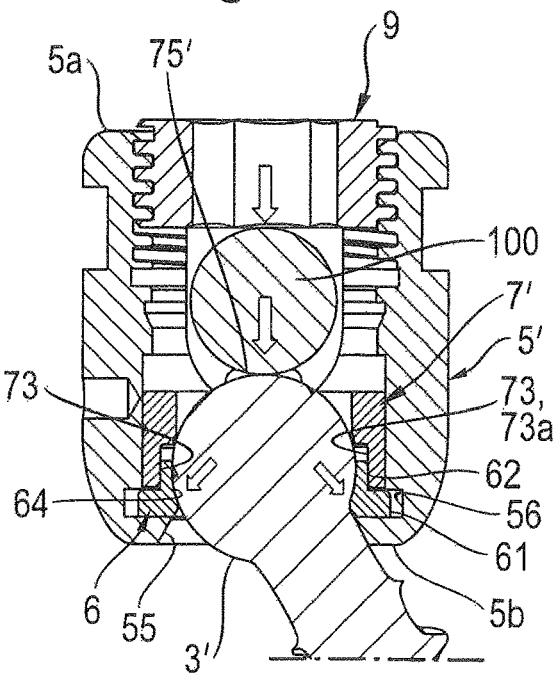
FIG. 20D shows a step of tightening a fixation element and locking of the head of the anchoring element at a selected orientation with pressure forces exerted, according to the second embodiment.

As shown in FIG. 20D, which corresponds to the state depicted in FIG. 13C with regard to the first embodiment, final locking is accomplished by attaching and tightening the fixation element 9 at the top end 5*a* of the receiving part 5', thereby exerting a pressure force onto the rod 100 received in the rod receiving portion 75' of the locking element 7'. The rod 100 transfers the pressure force onto the spherical head 3'. The spherical head 3' is adversely pressed against the retainer element 6, which may neither expand nor release the head 3 because the second engagement portion 62 is radially bound by the inner wall 73*a* of the cavity 73. Nor may the retainer element 6 axially move further towards the opening 55 because the first engagement portion 61 is received in the annular groove of the engagement structure 56.

The bone anchoring device of the first and second embodiments as a whole or in parts may be made of a bio-compatible material, such as a bio-compatible metal or a metal alloy, for example titanium, stainless steel, a nickel-titanium alloy, for example nitinol, or of bio-compatible plastic materials, such as, for example, polyetheretherketon (PEEK) or of a bio-compatible ceramic material. In particular, the retainer and/or locking elements may be made of a superelastic nickel-titanium alloy or of beta titanium.

Further modifications of the coupling assembly and polyaxial bone anchoring device may be contemplated.

Other possible modifications of the receiving part may include, for example, instead of the U-shaped recess being perpendicular to the central axis, a recess for the rod may be inclined, open to the side, or in the form of a closed channel. Other kinds of locking devices including outer nuts, outer caps, bayonet locking devices, and others are also possible as noted above. In particular, a two-part locking device that includes a first locking element that exerts pressure via the pressure element onto the head and the second locking element that exerts pressure only onto the rod to lock the head and the rod independently, may also be used. In some embodiments, the inner surface portion of the locking element that contacts the head (as in the first embodiment) may not necessarily be spherically-shaped. The inner surface portion may have any other shape that is suitable to exert pressure onto the head. Also, the design of the locking element can be different and is not limited to the specific design shown in the first or second embodiments.

Instead of the pin for retaining the pressure element and for aligning the pressure element with respect to the channel for receiving the rod of the receiving part, other retaining mechanisms can be used.

In the above embodiments, the accommodation space is of a substantially cylindrical shape. However, other shapes or deviations from a cylindrical may be possible as well which allow a locking element (having corresponding shapes or deviations) to move between the respective first and second positions connected with the unlocked and locked states.

In the above embodiments, the locking element is shown as either being provided with arms and shoulders to effect a pre-locked state or without arms. However, both embodiments may also be formed without arms, or with arms, and with corresponding functions, respectively.

The coupling assembly of the above or further embodiments including the retainer and the locking element (embodied as a pressure element or not) may be in situ snapped-on to the head 3, 3' of anchoring element 1, 1' when the anchoring element is inserted into a bone, e.g., a vertebra, or in a not yet implanted state.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling assembly for coupling a rod to a bone anchoring element, the coupling assembly comprising:
   a receiving part having a first end, a second end below the first end, a central axis extending through the first end and the second end, an accommodation space for accommodating a head of the bone anchoring element, the accommodation space having an opening at the second end sized to permit insertion of the head into the receiving part, and a recess at the first end for receiving the rod;
   a retainer element positionable at least partially in the accommodation space and radially expandable to facilitate insertion of the head; and
   a locking element positionable at least partially in the accommodation space, the locking element having a lower end region with an inner surface that has a substantially constant inner width as the inner surface extends axially;
   wherein when the retainer element and the locking element are in the receiving part, the lower end region of the locking element is directly engageable with the retainer element, and the locking element is movable to adjust the coupling assembly from a first configuration where the retainer element is expandable for inserting the head, to a second configuration where a vertical surface that extends substantially parallel to the central axis restricts radial expansion of the retainer element to prevent release of the inserted head.

2. The coupling assembly of claim 1, wherein the retainer element defines an open or closed ring-shape.

3. The coupling assembly of claim 1, wherein the retainer element includes one or more slits configured to allow the retainer element to expand.

4. The coupling assembly of claim 1, wherein the retainer element defines a hollow spherical segment-shaped portion configured to receive the head.

5. The coupling assembly of claim 1, wherein the inner surface of the locking element forms the vertical surface that restricts the radial expansion of the retainer element in the second configuration.

6. The coupling assembly of claim 1, wherein the locking element is a pressure element configured to receive and transfer a pressure force from a fixation element and/or the rod received in the recess of the receiving part to lock the inserted head.

7. The coupling assembly of claim 6, wherein the the locking element defines an inner hollow spherical segment-shaped recess configured to receive the inserted head.

8. The coupling assembly of claim 1, wherein the locking element comprises a rod receiving portion configured to receive the rod.

9. The coupling assembly of claim 1, wherein the locking element comprises a first surface configured to engage a second surface of the receiving part when the coupling assembly is in the second configuration to prevent adjustment of the coupling assembly back to the first configuration.

10. The coupling assembly of claim 1, wherein the locking element is configured to directly engage the inserted head.

11. The coupling assembly of claim 1, wherein an axial height of the locking element is the same in the first and second configurations.

12. The coupling assembly of claim 1, wherein the coupling assembly can remain at the first configuration without any external forces acting on the coupling assembly.

13. The coupling assembly of claim 1, wherein the lower end region of the locking element engages the retainer element to adjust the coupling assembly from the first configuration to the second configuration.

14. A polyaxial bone anchoring device comprising:
   a bone anchoring element having a shank for anchoring to bone and a head; and
   a coupling assembly for coupling a rod to a bone anchoring element, the coupling assembly comprising:
      a receiving part having a first end, a second end below the first end, a central axis extending through the first end and the second end, an accommodation space for accommodating the head, the accommodation space having an opening at the second end sized to permit insertion of the head into the receiving part, and a recess at the first end for receiving the rod;
      a retainer element positionable at least partially in the accommodation space and radially expandable to facilitate insertion of the head; and
      a locking element positionable at least partially in the accommodation space;
      wherein when the head, the retainer element, and the locking element are in the receiving part at a first configuration, an upper surface at an end of the locking element is configured to engage another surface of the coupling assembly to restrict further upward movement of the locking element relative to the receiving part, while the retainer element is expandable for inserting the head;

wherein the locking element is movable to adjust the coupling assembly from the first configuration to a second configuration where radial expansion of the retainer element is restricted to prevent release of the head, and wherein an axial height of the locking element is the same in the first and second configurations; and wherein the head is configured to extend to an axial position that is closer to the first end of the receiving part than the retainer element and the upper surface of the locking element are to the first end of the receiving part.

15. The polyaxial bone anchoring device of claim 14, wherein the locking element comprises a rod receiving portion formed on the upper surface to receive the rod.

16. The polyaxial bone anchoring device of claim 14, wherein the locking element is configured to directly engage the head in the receiving part.

17. A polyaxial bone anchoring device comprising:

a bone anchoring element having a shank for anchoring to bone and a head; and a coupling assembly for coupling a rod to a bone anchoring element, the coupling assembly comprising:

a receiving part having a first end, a second end, a central axis extending through the first end and the second end, an accommodation space for accommodating the head, the accommodation space having an opening at the second end sized to permit insertion of the head into the receiving part, and a recess at the first end for receiving the rod;

a retainer element positionable at least partially in the accommodation space and radially expandable to facilitate insertion of the head; and a locking element positionable at least partially in the accommodation space, the locking element comprising a first region directly engageable with the retainer element and a second region directly engageable with the head;

wherein when the head, the retainer element, and the locking element are in the receiving part, the locking element is movable to adjust the coupling assembly from a first configuration where the retainer element is expandable for inserting the head, to a second configuration where the first region of the locking element surrounds at least part of the retainer element to directly block radial expansion of the retainer element and prevent release of the head.

18. The polyaxial bone anchoring device of claim 17, wherein the retainer element comprises projections extending from an upper surface of the retainer element, and wherein the locking element is configured to surround the projections when the coupling assembly is at the second configuration.

19. The polyaxial bone anchoring device of claim 17, wherein the locking element is monolithic.

20. The polyaxial bone anchoring device of claim 17, wherein the locking element defines an inner hollow spherical segment-shaped recess configured to receive the head.

\* \* \* \* \*

UNITED STATES PATENT AND TRADEMARK OFFICE
CERTIFICATE OF CORRECTION

| | | |
|---|---|---|
| PATENT NO. | : 11,045,230 B2 | Page 1 of 1 |
| APPLICATION NO. | : 16/518339 | |
| DATED | : June 29, 2021 | |
| INVENTOR(S) | : Biedermann et al. | |

It is certified that error appears in the above-identified patent and that said Letters Patent is hereby corrected as shown below:

In the Claims

Column 14, Line 21, Claim 7      delete "the the" and insert -- the --

Signed and Sealed this
Twelfth Day of July, 2022

Katherine Kelly Vidal
*Director of the United States Patent and Trademark Office*